United States Patent
Ilekti et al.

(10) Patent No.: US 11,771,639 B2
(45) Date of Patent: Oct. 3, 2023

(54) AQUEOUS COMPOSITION COMPRISING A CATIONIC CELLULOSIC POLYMER, AN ANIONIC SURFACTANT COMPRISING AT LEAST ONE CATIONIC COUNTERION, A FATTY PHASE AND A PIGMENT

(71) Applicant: L'OREAL, Paris (FR)

(72) Inventors: Philippe Ilekti, Chevilly Larue (FR); Grégory Plos, Chevilly Larue (FR); Mohamed Boularas, Chevilly Larue (FR); Sylvie Poret Fristot, Chevilly Larue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/784,995

(22) PCT Filed: Dec. 11, 2020

(86) PCT No.: PCT/EP2020/085796
§ 371 (c)(1),
(2) Date: Jun. 13, 2022

(87) PCT Pub. No.: WO2021/122383
PCT Pub. Date: Jun. 24, 2021

(65) Prior Publication Data
US 2023/0037007 A1 Feb. 2, 2023

(30) Foreign Application Priority Data
Dec. 16, 2019 (FR) ........................ 1914479

(51) Int. Cl.
*A61Q 1/10* (2006.01)
*A61K 8/81* (2006.01)
*A61K 8/41* (2006.01)
*A61K 8/46* (2006.01)
*A61K 8/55* (2006.01)
*A61K 8/92* (2006.01)
*A61Q 5/10* (2006.01)

(52) U.S. Cl.
CPC ............ *A61K 8/8105* (2013.01); *A61K 8/416* (2013.01); *A61K 8/466* (2013.01); *A61K 8/55* (2013.01); *A61K 8/8147* (2013.01); *A61K 8/92* (2013.01); *A61Q 1/10* (2013.01); *A61Q 5/10* (2013.01); *A61K 2800/43* (2013.01)

(58) Field of Classification Search
CPC ...... A61K 8/8105; A61K 8/416; A61K 8/466; A61K 8/55; A61K 8/8147; A61K 8/92; A61K 2800/43; A61K 2800/5424; A61K 2800/5426; A61K 8/19; A61K 8/29; A61K 8/342; A61K 8/361; A61K 8/442; A61K 8/731; A61K 8/817; A61K 8/922; A61K 8/927; A61Q 1/10; A61Q 5/10

USPC ............................................. 424/70.7
See application file for complete search history.

(56) References Cited

U.S. PATENT DOCUMENTS

| | | | |
|---|---|---|---|
| 4,871,536 A | 10/1989 | Arraudeau et al. | |
| 5,876,704 A | 3/1999 | Collin et al. | |
| 6,534,047 B1 | 3/2003 | Bodelin | |
| RE38,362 E | 12/2003 | Collin et al. | |
| 2006/0083696 A1 | 4/2006 | Yu et al. | |
| 2007/0212316 A1* | 9/2007 | Feng | A61K 8/927 424/70.7 |
| 2009/0020133 A1 | 1/2009 | Gueret | |
| 2010/0086507 A1 | 4/2010 | Gueret | |
| 2014/0328786 A1* | 11/2014 | Ilekti | A61K 8/4946 424/70.13 |

FOREIGN PATENT DOCUMENTS

| | | | |
|---|---|---|---|
| CN | 101032455 A | 9/2007 | |
| EP | 1 064 919 A1 | 1/2001 | |
| EP | 1 647 268 A1 | 4/2006 | |
| EP | 1 674 076 A2 | 6/2006 | |
| EP | 1 832 227 A1 | 9/2007 | |
| FR | 2 528 699 A1 | 12/1983 | |
| FR | 3044896 A1 * | 6/2017 | .............. A61K 8/36 |

OTHER PUBLICATIONS

International Search Report dated Jan. 26, 2021 in PCT/EP2020/085796 filed on Dec. 11, 2020, 6 pages.
CN Office Action dated May 16, 2023 from related CN Patent Application No. 202080086393.6 filed Dec. 11, 2020; (No. Translation Available); 9 pages.

* cited by examiner

*Primary Examiner* — Eisa B Elhilo
(74) *Attorney, Agent, or Firm* — WOMBLE BOND DICKINSON (US) LLP

(57) ABSTRACT

The present application relates to a composition comprising, notably in a physiologically acceptable medium: •a. water; and•b. at least one cellulosic cationic polymer (CP); and•c. at least one anionic polymer (AP) chosen from methacrylic acid homopolymer salts; and•d. at least one anionic surfactant comprising at least one cationic counterion; and•e. a fatty phase; and•f. at least one pigment; the weight ratio of the total amount of cellulosic cationic polymer(s)/the sum of the total amount of cellulosic cationic polymer(s) and of the total amount of anionic polymer(s) ranging from 40% to 80%, preferably from 60% to 70%; the weight ratio of the sum of the total amount of cellulosic cationic polymer(s) and of the total amount of anionic polymer(s)/the amount of water ranging from 5% to 20%. The invention also relates to a process for coating keratin materials, in particular the skin, notably the contour of the eyes, eyelashes or eyebrows, and keratin fibers, such as the eyelashes and/or the eyebrows, comprising a step of applying to said keratin materials at least one composition as defined above.

19 Claims, No Drawings

AQUEOUS COMPOSITION COMPRISING A CATIONIC CELLULOSIC POLYMER, AN ANIONIC SURFACTANT COMPRISING AT LEAST ONE CATIONIC COUNTERION, A FATTY PHASE AND A PIGMENT

TECHNICAL FIELD

The present invention relates to compositions for making up and/or caring for human keratin materials, such as the skin, and keratin fibers such as the eyelashes and eyebrows. It likewise relates to a process for making up and/or caring for said human keratin materials, consisting in applying the composition according to the invention.

In the area of eye makeup products, aqueous products make it possible to obtain high makeup performance results. However, the wear property of these products is not very popular with consumers because their deposit is water sensitive. Furthermore, water-resistant (waterproof) anhydrous compositions and latex-rich (smudgeproof) aqueous compositions are known for their high wear property, but these compositions are not entirely satisfactory in terms of makeup removal.

There is a need to find new aqueous compositions for making up the contour of the eyes, the eyelashes and/or the eyebrows and the contour thereof which make it possible to obtain good makeup performance results and a good wear property and which can be easily removed by a water-based makeup removal product.

In the course of its research, the applicant has discovered, unexpectedly, that this objective is achieved by using a composition comprising, notably in a physiologically acceptable medium:
a. water; and
b. at least one cellulosic cationic polymer (CP); and
c. at least one anionic polymer (AP) chosen from methacrylic acid homopolymer salts; and
d. at least one anionic surfactant comprising at least one cationic counterion; and
e. a fatty phase; and
f. at least one pigment;
the weight ratio of the total amount of cellulosic cationic polymer(s)/the sum of the total amount of cellulosic cationic polymer(s) and of the total amount of anionic polymer(s) ranging from 40% to 70%, preferably from 60% to 70%;
the weight ratio of the sum of the total amount of cationic polymer(s) and of the total amount of anionic polymer(s)/the amount of water ranging from 5% to 20%.

The applicant has discovered, surprisingly, that the compositions according to the invention are macroscopically homogeneous (only 1 phase visible to the naked eye), have an excellent wear property and can be easily removed by a water-based makeup removal product.

This discovery forms the basis of the invention.

SUBJECTS OF THE INVENTION

Thus, according to one of its aspects, the present invention relates to a composition comprising, notably in a physiologically acceptable medium:
a. water; and
b. at least one cellulosic cationic polymer (CP); and
c. at least one anionic polymer (AP) chosen from methacrylic acid homopolymer salts; and
d. at least one anionic surfactant comprising at least one cationic counterion; and
e. a fatty phase; and
f. at least one pigment;
the weight ratio of the total amount of cellulosic cationic polymer(s)/the sum of the total amount of cellulosic cationic polymer(s) and of the total amount of anionic polymer(s) ranging from 40% to 70%, preferably from 60% to 70%;
the weight ratio of the sum of the total amount of cellulosic cationic polymer(s) and of the total amount of anionic polymer(s)/the amount of water ranging from 5% to 20%.

A second subject of the present invention is a cosmetic process for making up and/or caring for human keratin materials, such as the skin, notably the contour of the eyes, the contour of the eyelashes, the contour of the eyebrows; keratin fibers such as the eyelashes and the eyebrows, consisting in applying to said keratin materials a composition as defined above.

Definitions

In the context of the present invention, the term "keratin material" is notably intended to mean the skin, notably the contour of the eyes, the contour of the eyelashes, the contour of the eyebrows; keratin fibers such as the eyelashes and the eyebrows.

The term "physiologically acceptable" is intended to mean compatible with the skin and/or its integuments, which has a pleasant color, odor and feel, and which does not cause any unacceptable discomfort (stinging or tautness) liable to discourage the consumer from using this composition.

The term "cationic polymer" is intended to mean any polymer comprising in its structure positively charged ionic groups associated with negative counterions.

The term "anionic polymer" is intended to mean any polymer comprising in its structure negatively charged ionic groups associated with positive counterions.

Aqueous Phase

The composition according to the invention comprises an aqueous phase.

The term "aqueous phase" is intended to mean a phase comprising water and also optionally all the solvents and ingredients that are water-soluble or water-miscible (water-miscibility greater than 50% by weight at 25° C.), for instance lower monoalcohols containing from 1 to 5 carbon atoms such as ethanol or isopropanol, glycols containing from 3 to 8 carbon atoms such as propylene glycol, 1,3-butylene glycol, caprylyl glycol, pentylene glycol and dipropylene glycol.

The aqueous phase may contain a demineralized water or alternatively a floral water such as cornflower water and/or a mineral water such as Vittel water, Lucas water or La Roche Posay water and/or a spring water.

The water is preferably present in a concentration ranging from 30% to 70% by weight relative to the total weight of the composition, preferably ranging from 40% to 60% by weight relative to the total weight of the composition, preferably ranging from 45% to 55% by weight relative to the total weight of the composition.

Cellulosic Cationic Polymer

The composition according to the invention comprises at least one cationic polymer chosen from cellulosic cationic polymers.

According to the invention, the term "cellulosic polymer" means any polysaccharide polymer bearing in its structure linear sequences of anhydroglucopyranose (AGU) residues linked together via β-(1,4) glycosidic bonds. The repeating unit is the cellobiose dimer. The AGUs are in chair conformation and bear 3 hydroxyl functions: two secondary alcohols (in position 2 and 3) and one primary alcohol (in position 6). The polymers thus formed combine together via intermolecular bonds of hydrogen bond type, thus giving the cellulose a fibrillar structure (about 1500 molecules per fiber).

The degree of polymerization differs enormously depending on the origin of the cellulose; its value may range from a few hundred to several tens of thousands.

Cellulose has the following chemical structure:

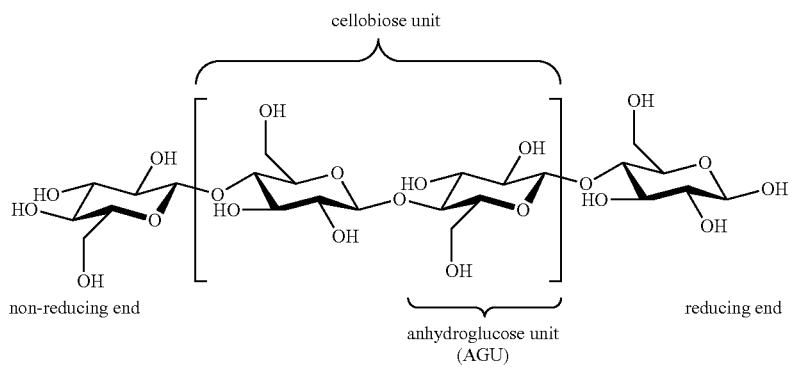

Among the cellulosic cationic polymers, mention may be made of:
1. quaternary ammoniums of hydroxy($C_1$-$C_4$)alkyl cellulose that has reacted with an epoxide (notably epichlorohydrin) substituted by a trimethylammonium group as described in French patent FR1 492 597. Mention may more particularly be made of the quaternary ammonium salts of hydroxyethyl cellulose and of 2,3-epoxypropyltrimonium having the INCI name: POLYQUATERNIUM-10 such as the commercial products CELQUAT SC140C®, CELQUAT SC240C®, CELQUAT 230M® from the company Nouryon Chemicals; the commercial products UCARE POLYMER JR 400®, UCARE POLYMER JR 125®, UCARE POLYMER JR 30 M®, UCARE POLYMER LR 400®, UCARE POLYMER LR30M® from the company Dow Chemical Company.
2. hydroxy($C_1$-$C_4$)alkyl celluloses grafted by a methacryloylethyltrimethylammonium, methacrylamidopropyltrimethylammonium or dimethyldiallylammonium salt (chloride) with the INCI name: POLYQUATERNIUM-4 and as described in U.S. Pat. No. 4,131,576. The commercial products corresponding to this definition are, more particularly, the products sold under the names "Celquat L 200®" and "Celquat H 100®" by the company National Starch;
3. mixtures thereof.

Use will more particularly be made of a quaternary ammonium salt of hydroxyethyl cellulose and of 2,3-epoxypropyltrimonium having the INCI name: POLYQUATERNIUM-10.

The cellulosic cationic polymer(s) in accordance with the invention is (are) preferably present in an active material concentration ranging from 1.0% to 5.0% by weight, more particularly from 2.0% to 3.5% by weight, relative to the total weight of said composition.

Anionic Polymer

The composition according to the invention comprises at least one anionic polymer chosen from the inorganic or organic salts of methacrylic acid homopolymer, notably the alkali metal (i.e.: sodium, potassium) salts, the ammonia salts ($NH_4^+$), the amine or amino alcohol organic salts (i.e.: triethanolamine, 2-amino-2-methyl-1,3-propanediol).

Use will be made more particularly of the sodium salts of methacrylic acid homopolymer, having the INCI name: Sodium polymethacrylate sold under the names Darvan 7-N® by the company Vanderbilt Minerals LLC and Syntran EX150-19® by the company Interpolymer Corporation.

The anionic polymer(s) in accordance with the invention is (are) preferably present in an active material concentration ranging from 1.0% to 5.0% by weight, more particularly from 1.4% to 3.0% by weight, relative to the total weight of said composition.

Anionic Surfactant

The composition according to the invention comprises at least one anionic surfactant comprising at least one cationic counterion, preferably at least one anionic surfactant in a form neutralized by said cationic counterion (salt).

For the purposes of the present invention, the term "surfactant" is intended to mean an amphiphilic chemical compound, i.e. one which has in its structure two parts of different polarity. Generally, one is lipophilic (soluble or dispersible in an oily phase). The other is hydrophilic (soluble or dispersible in water). Surfactants are characterized by their HLB (hydrophilic lipophilic balance) value, the HLB being the ratio between the hydrophilic part and the lipophilic part in the molecule. The term "HLB" is well known to those skilled in the art and is described, for example, in "The HLB system. A time-saving guide to Emulsifier Selection" (published by ICI Americas Inc., 1984).

According to one preferential form of the invention, the anionic surfactants in accordance with the invention have an HLB greater than or equal to 8. The HLB of the anionic surfactant(s) used according to the invention may be determined by the Griffin method.

The term "anionic surfactant" is intended to mean any negatively charged amphiphilic molecule.

The term "cationic counterion" is intended to mean any positively charged ion or ionic group capable of neutralizing said anionic surfactant and of forming a salt.

The anionic surfactant(s) in accordance with the invention is (are) preferably chosen from:

i. alkyl phosphates;
ii. alkyl sulfates, and in particular alkyl ether sulfates, alkylamido ether sulfates, alkylaryl polyether sulfates and monoglyceride sulfates;
iii. alkyl sulfonates, alkylamide sulfonates, alkylaryl sulfonates, α-olefin sulfonates, paraffin sulfonates;
iv. alkyl sulfosuccinates, alkyl ether sulfosuccinates, alkylamide sulfosuccinates; alkyl sulfosuccinamates;
v. alkyl sulfoacetates;
vi. acyl sarcosinates, acyl glutamates, acyl isethionates, N-acyl taurates and acyl lactylates;
vii. alkylpolyglycoside carboxylic esters, such as alkylglucoside citrates, alkylpolyglycoside tartrates, alkylpolyglycoside sulfosuccinates or alkylpolyglycoside sulfosuccinamates;
viii. fatty acids, in particular oleic acid, ricinoleic acid, palmitic acid or stearic acid, coconut oil acid or hydrogenated coconut oil acid;
ix. alkyl-D-galactosiduronic acids;
x. polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids, in particular those containing from 2 to 50 alkylene oxide and in particular ethylene oxide groups;
xi. mixtures thereof.

The anionic surfactant(s) in accordance with the invention is (are) preferably present in a total content of greater than or equal to 2% by weight relative to the total weight of the composition, preferably ranging from 2% to 10% and better still from 3% to 8% by weight, relative to the total weight of the composition.

The cationic counterion(s) in accordance with the invention is (are) chosen from a cation of mineral origin, in particular chosen from alkali metal (sodium, potassium) cations, the ammonium ion ($NH_4^+$) or organic cations.

Said organic cationic counterion(s) is (are) preferably chosen from amines and amino alcohols.

According to one particular form of the invention, said organic cationic counterion(s) comprise(s) a primary (poly)hydroxyalkylamine.

The term "primary (poly)hydroxyalkylamine" is intended to mean in particular a primary dihydroxyalkylamine, it being understood that the term "primary" refers to a primary amine function, i.e. —$NH_2$, and the alkyl group being a linear or branched $C_1$-$C_8$, preferably branched $C_4$, hydrocarbon-based chain, such as 1,3-dihydroxy-2-methylpropyl (also known as aminomethylpropanediol or AMPD).

The total content of cationic counterion(s) is preferably greater than or equal to 0.01%, more preferentially inclusively between 0.1% and 4.0% by weight, better still between 0.5% and 3.0% by weight, relative to the total weight of the composition.

According to one particular form of the invention, said anionic surfactant(s) is (are) chosen from $C_{12}$-$C_{22}$, preferably $C_{14}$-$C_{18}$, fatty acids, more particularly the salt of stearic acid and of the cationic counterion aminomethylpropanediol;

alkyl phosphates, preferably in a form neutralized by a cationic counterion of an alkali metal and more particularly potassium. By way of example, mention may be made of the anionic surfactant in a form neutralized by its potassium cationic counterion, having the INCI name: Potassium Cetyl Phosphate, such as the commercial product sold under the name Amphisol K® by the company DSM Nutritional Products Europe Ltd;

acyl glutamates, preferably in a form neutralized by a cationic counterion of an alkali metal and more particularly sodium. By way of example, mention may be made of the anionic surfactant in a form neutralized by its sodium cationic counterion, having the INCI name: Sodium Stearoyl Glutamate, such as the commercial product sold under the name Amisoft® HS-11P by the company Ajinomoto OmniChem;

mixtures thereof.

Fatty Phase

The composition(s) according to the invention comprise a fatty phase, which is preferably a dispersed fatty phase.

The fatty phase may be present in a content of between 5% and 45% by weight, preferably between 10% and 45% by weight, better still from 10% to 40% by weight, relative to the total weight of the composition.

The dispersed fatty phase may comprise at least one wax and/or at least one pasty fatty substance and/or at least one oil.

a) Waxes

Preferably, the composition(s) according to the invention comprise at least one wax. This wax makes it possible to obtain thick, charging textures.

The term "wax" is intended to mean a lipophilic compound that is solid at ambient temperature (25° C.), which may or may not be deformable, which has a reversible solid/liquid change of state, and which has a melting point of greater than or equal to 40° C. that can range up to 120° C. In particular, the waxes suitable for the invention can have a melting point of greater than or equal to 45° C., in particular greater than or equal to 55° C.

The term "lipophilic compound" is intended to mean a compound which has an acid number and a hydroxyl number of less than 150 mg KOH/g.

For the purposes of the invention, the melting point corresponds to the temperature of the most endothermic peak observed on thermal analysis (DSC) as described in the standard ISO 11357-3; 1999. The melting point of the wax may be measured using a differential scanning calorimeter (DSC), for example the calorimeter sold under the name MDSC 2920® by the company TA Instruments.

The measuring protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes may be hydrocarbon-based waxes, silicone waxes and/or fluoro waxes, and may be of plant, mineral, animal and/or synthetic origin.

The wax may be present in a content ranging from 5% to 45% by weight relative to the total weight of the composition, better still from 8% to 40% by weight and even better still from 10% to 40% by weight.

As wax, use may in particular be made of hydrocarbon-based waxes such as beeswax, lanolin wax; rice wax, carnauba wax, candelilla wax, ouricury wax, Japan wax, berry wax, shellac wax and sumac wax; montan wax.

Mention may also be made of waxes obtained by catalytic hydrogenation of animal or plant oils containing linear or branched 08-$C_{32}$ fatty chains.

Among these waxes, mention may especially be made of hydrogenated jojoba oil, hydrogenated palm oil, hydrogenated sunflower oil, hydrogenated castor oil, hydrogenated coconut oil, hydrogenated lanolin oil, bis(1,1,1-trimethylolpropane) tetrastearate sold under the name HEST 2T-4S® by the company Heterene and bis(1,1,1-trimethylolpropane) tetrabehenate sold under the name HEST 21-4B® by the company Heterene.

Use may also be made of the wax obtained by hydrogenation of olive oil esterified with stearyl alcohol, sold under the name Phytowax Olive 18L57®, or else the waxes obtained by hydrogenation of castor oil esterified with cetyl alcohol, sold under the names Phytowax Ricin 16L64® and 22L73®, by the company Sophim.

Such waxes are described in application FR-A-2 792 190.

Use may also be made of a $C_{20}$-$C_{40}$ alkyl (hydroxystearyloxy)stearate (the alkyl group comprising from 20 to 40 carbon atoms), alone or as a mixture, in particular a $C_{20}$-$C_{40}$ alkyl 12-(12'-hydroxystearoyloxy)stearate, of formula (I):

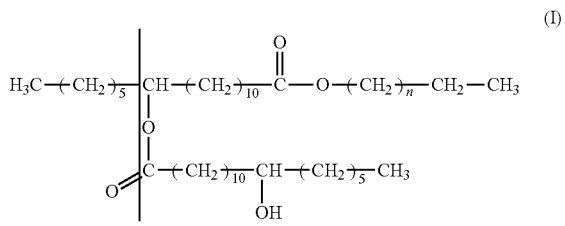

wherein n is an integer ranging from 18 to 38, or a mixture of compounds of formula (1). Such a tacky wax is notably sold under the names Kester Wax K 82 P and Kester Wax K 80 P by the company Koster Keunen.

Mention may be made of microcrystalline waxes, paraffins and ozokerite, polyethylene waxes, waxes obtained by Fischer-Tropsch synthesis and waxy copolymers and also esters thereof; silicone waxes and fluoro waxes.

Mention may be made of the linear fatty acid monoesters of formula (1) below:

in which $R_3$ and $R_4$ are linear and saturated and have, independently of each other, a number of carbon atoms greater than or equal to 20, with $R_3$ representing an acyl radical, and $R_4$ representing an alkyl radical.

In particular, the fatty acid monoester according to the invention is chosen from arachidyl arachidate and behenyl behenate and more particularly behenyl behenate.

According to one preferred mode, use will be made of a wax chosen from beeswax, carnauba wax, cetyl alcohol, behenyl behenate, and mixtures thereof.

b) Pasty Fatty Substance

For the purposes of the present invention, the term "pasty fatty substance" is intended to mean a lipophilic fatty compound with a reversible solid/liquid change of state, which comprises, at a temperature of 23° C., a liquid fraction and a solid fraction. In other words, the starting melting point of the pasty compound may be less than 23° C. The liquid fraction of the pasty compound measured at 23° C. may represent 9% to 97% by weight of the compound. This fraction that is liquid at 23° C. preferably represents between 15% and 85% and more preferably between 40% and 85% by weight.

Preferably, the pasty fatty substances have an end melting point of less than 60° C.

Preferably, the pasty fatty substances have a hardness of less than or equal to 6 MPa.

Preferably, the pasty fatty substances have, in the solid state, a crystalline organization, which is visible by X-ray diffraction characterization.

For the purposes of the invention, the melting point corresponds to the temperature of the most endothermic peak observed in thermal analysis (DSC) as described in the standard ISO 11357-3; 1999. The melting point of a pasty substance can be measured using a differential scanning calorimeter (DSC), for example the calorimeter sold under the name DSC 02000® by the company TA Instruments.

As regards the measurement of the melting point and the determination of the end melting point, the sample preparation and measurement protocols are as follows:

A sample of 5 mg of pasty fatty substance, preheated to 80° C. and withdrawn with magnetic stirring using a spatula that is also heated, is placed in a hermetic aluminum capsule, or a crucible. Two tests are performed to ensure the reproducibility of the results. The measurements are performed on the abovementioned calorimeter. The oven is flushed with nitrogen. Cooling is performed by an RCS 90 heat exchanger. The sample is then subjected to the following protocol by being first of all brought to a temperature of 20° C., then subjected to a first temperature rise ranging from 20° C. to 80° C., at the heating rate of 5° C./minute, and then is cooled from 80° C. to −80° C. at a cooling rate of 5° C./minute and is finally subjected to a second temperature rise ranging from −80° C. to 80° C. at a heating rate of 5° C./minute. During the second temperature rise, the variation in the difference between the power absorbed by the empty crucible and by the crucible containing the sample of pasty substance or wax as a function of the temperature is measured. The melting point of the compound is the temperature value corresponding to the top of the peak of the curve representing the variation in the difference in power absorbed as a function of the temperature. The end melting point corresponds to the temperature at which 95% of the sample has melted. The liquid fraction by weight of the pasty compound at 23° C. is equal to the ratio of the heat of fusion consumed at 23° C. to the heat of fusion of the pasty compound. The heat of fusion of the pasty compound is the heat consumed by the compound in order to pass from the solid state to the liquid state. The pasty compound is said to be in the solid state when all of its mass is in crystalline solid form. The pasty compound is said to be in the liquid state when all of its mass is in liquid form. The heat of fusion of the pasty compound is equal to the integral of the entire melting curve obtained using the abovementioned calorimeter, with a temperature rise of 5 or 10° C./minute, according to standard ISO 11357-3:1999. The heat of fusion of the pasty compound is the amount of energy required to make the compound change from the solid state to the liquid state. It is expressed in J/g. The heat of fusion consumed at 23° C. is the amount of energy absorbed by the sample to change from the solid state to the state that it has at 23° C., constituted of a liquid fraction and a solid fraction. The liquid fraction of the pasty compound measured at 32° C. preferably represents from 30% to 100% by weight of the compound, preferably from 50% to 100% by weight and more preferably from 60% to 100% by weight of the compound. When the liquid fraction of the pasty compound measured at 32° C. is equal to 100%, the temperature of the end of the melting range of the pasty compound is less than or equal to 32° C. The liquid fraction of the pasty compound measured at 32° C. is equal to the ratio of the heat of fusion consumed at 32° C. to the heat of fusion of the pasty compound. The heat of fusion consumed at 32° C. is calculated in the same way as the heat of fusion consumed at 23° C.

As regards the measurement of the hardness, the sample preparation and measurement protocols are as follows:

The pasty fatty substance is placed in a mold 75 mm in diameter, which is filled to about 75% of its height. In order to overcome the thermal history and to control the crystallization, the mold is placed in a Votsch VC0018 programmable oven, where it is first placed at a temperature of 80° C. for 60 minutes, then cooled from 80° C. to 0° C. at a cooling rate of 5° C./minute, and then left at the stabilized temperature of 0° C. for 60 minutes, and then subjected to a temperature rise ranging from 0° C. to 20° C., at a heating rate of 5° C./minute, and then left at the stabilized temperature of 20° C. for 180 minutes. The compression force measurement is taken using a TA/TX2i texturometer from Swantech.

The spindle used is chosen according to the texture:
cylindrical steel spindle 2 mm in diameter for very rigid starting materials;
cylindrical steel spindle 12 mm in diameter for sparingly rigid starting materials.

The measurement comprises three steps:
a first step after automatic detection of the surface of the sample, wherein the spindle moves at a measuring speed of 0.1 mm/second, and penetrates into the pasty fatty substance to a penetration depth of 0.3 mm, and the software notes the maximum force value reached;
a second step, known as relaxation, wherein the spindle remains in this position for one second and the force is noted after 1 second of relaxation;
a third step, known as withdrawal, wherein the spindle returns to its original position at a speed of 1 mm/second, and the withdrawal energy of the probe (negative force) is noted. The hardness value measured during the first step corresponds to the maximum compression force measured in newtons divided by the area of the texturometer cylinder expressed in mm2 in contact with the pasty fatty substance. The hardness value obtained is expressed in megapascals or MPa.

The pasty fatty substance is preferably chosen from synthetic compounds and compounds of plant origin. A pasty compound may be obtained via synthesis from starting materials of plant origin.
The pasty compound is advantageously chosen from:
lanolin and derivatives thereof;
petroleum jelly, in particular that for which the INCI name is Petrolatum and which is sold under the name Ultima White PET USP® by the company Penreco;
polyol ethers chosen from ethers of pentaerythritol and of polyalkylene glycol, ethers of fatty alcohol and of sugar, and mixtures thereof, the polyethylene glycol pentaerythrityl ether comprising 5 oxyethylene units (5 OE) (INCI name: PEG-5 Pentaerythrityl Ether), the polypropylene glycol pentaerythrityl ether comprising 5 oxypropylene (5 OP) units (INCI name: PPG-5 Pentaerythrityl Ether), and mixtures thereof, and more especially the PEG-5 Pentaerythrityl Ether, PPG-5 Pentaerythrityl Ether and soybean oil mixture sold under the Lanolide® name by Vevy, which is a mixture in which the constituents are in a 46/46/8 ratio by weight:
46% PEG-5 pentaerythrityl ether, 46% PPG-5 pentaerythrityl ether and 8% soybean oil;
polymeric or non-polymeric silicone compounds;
polymeric or non-polymeric fluoro compounds;
vinyl polymers, notably chosen from:
i) olefin homopolymers and copolymers;
ii) hydrogenated diene homopolymers and copolymers;
iii) linear or branched homopolymer or copolymer oligomers of alkyl (meth)acrylates preferably containing a $C_8$-$C_{30}$ alkyl group;
iv) homopolymer and copolymer oligomers of vinyl esters containing $C_8$-$C_{30}$ alkyl groups;
v) homopolymer and copolymer oligomers of vinyl ethers containing $C_8$-$C_{30}$ alkyl groups;
liposoluble polyethers resulting from polyetherification between one or more $C_2$-$C_{100}$ and preferably $C_2$-$050$ diols;
esters,
mixtures thereof.

The pasty compound is preferably a polymer, especially a hydrocarbon-based polymer.

Among the liposoluble polyethers that are particularly preferred are copolymers of ethylene oxide and/or of propylene oxide with $C_6$-$030$ long-chain alkylene oxides, more preferably still such that the weight ratio of the ethylene oxide and/or of propylene oxide to the alkylene oxides in the copolymer is from 5:95 to 70:30. In this family, mention will be made especially of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9® by AkzoNobel.

Among the esters, the following are notably preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, preferably such as bis-diglyceryl polyacyladipate-2 sold under the brand name Softisan 649® by the company Sasol,
the arachidyl propionate sold under the brand name Waxenol 801® by Alzo,
phytosterol esters,
fatty acid triglycerides and derivatives thereof, for instance triglycerides of fatty acids, which are notably $C_{10}$-$018$, and partially or totally hydrogenated such as those sold under the reference Softisan 100® by the company Sasol,
pentaerythritol esters,
esters of a diol dimer and of a diacid dimer, where appropriate esterified on their free alcohol or acid function(s) with acid or alcohol radicals, notably dimer dilinoleate esters; such esters may be chosen notably from the esters having the following INCI nomenclature: bis-behenyl/isostearyl/phytosteryl dimer dilinoleyl dimer dilinoleate (Plandool G®), phytosteryl/isostearyl/cetyl/stearyl/behenyl dimer dilinoleate (Plandool H® or Plandool S®),
mango butter, such as the product sold under the reference Lipex 203® by the company AarhusKarlshamn,
shea butter, in particular the product of which the INCI name is *Butyrospermum parkii* Butter, such as the product sold under the reference Sheasoft® by the company AarhusKarlshamn.

Among the pasty compounds, the following will preferably be chosen:
bis-behenyl/isostearyl/phytosteryl dilinoleyl dimer and bis-diglyceryl polyacyladipate-2,
hydrogenated castor oil dimer dilinoleate, for example Risocast-DA-L® sold by Kokyu Alcohol Kogyo, hydrogenated castor oil isostearate, for example Salacos HCIS® (V-L) sold by Nisshin Oil, mango butter, shea butter,
vinylpyrrolidone/eicosene copolymers, and a mixture or mixtures thereof.

c) Oils

The composition(s) according to the invention may comprise one or more non-aqueous oils or fatty substances that are liquid at ambient temperature (25° C.) and atmospheric pressure (760 mmHg).

The oil may be chosen from volatile oils and/or nonvolatile oils, and mixtures thereof.

The oil(s) may be present in the composition according to the invention in a content of less than 5% by weight and preferably from 0.5% to 3% by weight relative to the total weight of the composition.

For the purposes of the invention, the term "volatile oil" means an oil that is capable of evaporating on contact with the keratin fibers in less than one hour, at ambient temperature and atmospheric pressure. The volatile organic solvent (s) and volatile oils of the invention are volatile organic solvents and cosmetic oils that are liquid at ambient temperature, with a non-zero vapor pressure at ambient temperature and atmospheric pressure, ranging in particular from 0.13 Pa to 40 000 Pa (10-3 to 300 mmHg), in particular ranging from 1.3 Pa to 13 000 Pa (0.01 to 100 mmHg), and more particularly ranging from 1.3 Pa to 1300 Pa (0.01 to 10 mmHg). The term "nonvolatile oil" is intended to mean an oil that remains on the keratin fiber, at ambient temperature and atmospheric pressure, for at least several hours and that notably has a vapor pressure of less than 10-3 mmHg (0.13 Pa).

These oils may be hydrocarbon-based oils, silicone oils or fluoro oils, or mixtures thereof.

The term "hydrocarbon-based oil" is intended to mean an oil mainly containing hydrogen and carbon atoms and possibly oxygen, nitrogen, sulfur or phosphorus atoms. The volatile hydrocarbon-based oils may be chosen from hydrocarbon-based oils containing from 8 to 16 carbon atoms, and especially branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Other volatile hydrocarbon-based oils, for instance petroleum distillates, especially those sold under the name Shell Solt by Shell, may also be used. The volatile solvent is preferably chosen from volatile hydrocarbon-based oils containing from 8 to 16 carbon atoms, and mixtures thereof.

Volatile oils that may also be used include volatile silicones, for instance volatile linear or cyclic silicone oils, especially those with a viscosity 8 centistokes (8×10⁻⁶ m²/s) and especially containing from 2 to 7 silicon atoms, these silicones optionally comprising alkyl or alkoxy groups containing from 1 to 10 carbon atoms. Mention may in particular be made, as volatile silicone oils which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and mixtures thereof.

Mention may also be made of the volatile linear alkyltrisiloxane oils of general formula (I):

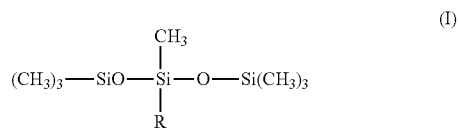

in which R represents an alkyl group containing from 2 to 4 carbon atoms and of which one or more hydrogen atoms may be substituted with a fluorine or chlorine atom.

Among the oils of general formula (I), mention may be made of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane corresponding to the oils of formula (I) for which R is, respectively, a butyl group, a propyl group or an ethyl group.

The composition(s) according to the invention may comprise at least one nonvolatile oil, chosen especially from nonvolatile hydrocarbon-based oils and/or silicone oils and/or fluoro oils.

As nonvolatile hydrocarbon-based oils, mention may notably be made of:
hydrocarbon-based oils of plant origin, such as fatty acid triesters of glycerol, the fatty acids of which may have varied chain lengths from $C_4$ to $C_{24}$, these chains possibly being linear or branched, and saturated or unsaturated; these oils are especially wheatgerm oil, sunflower oil, grapeseed oil, corn oil, apricot oil, castor oil, shea oil, avocado oil, olive oil, soybean oil, sweet almond oil, palm oil, cottonseed oil, hazelnut oil, macadamia oil, jojoba oil, alfalfa oil, poppy oil, pumpkin oil, sesame seed oil, marrow oil, rapeseed oil, blackcurrant oil, evening primrose oil, millet oil, barley oil, quinoa oil, rye oil, safflower oil, candlenut oil, passion flower oil and musk rose oil; or alternatively caprylic/capric acid triglycerides such as those sold by the company Stéarineries Dubois or those sold under the names Miglyol 810®, 812® and 818® by the company Dynamit Nobel;
linear or branched hydrocarbons, of mineral or synthetic origin, such as liquid paraffins and derivatives thereof, polydecenes, polybutenes, hydrogenated polyisobutene such as Parleam, or squalane;
synthetic ethers containing from 10 to 40 carbon atoms;
synthetic esters such as oils of formula $R_1COOR_2$ in which $R_1$ represents a linear or branched fatty acid residue containing from 1 to 40 carbon atoms and $R_2$ represents an in particular branched hydrocarbon-based chain containing from 1 to 40 carbon atoms, on condition that $R_1+R_2$ is 10, for instance purcellin oil (cetostearyl octanoate), isopropyl myristate, isopropyl palmitate, $C_{12}$ to $C_{15}$ alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearyl lactate and diisostearyl malate; and pentaerythritol esters;

fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol, 2-undecylpentadecanol;

higher fatty acids such as oleic acid, linoleic acid or linolenic acid; and mixtures thereof.

The nonvolatile silicone oils that may be used in the composition according to the invention may be nonvolatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

The fluoro oils that can be used in the invention are in particular fluorosilicone oils, fluoro polyethers and fluorosilicones as described in document EP-A-847 752.

Pigments

The composition according to the invention comprises at least one pigment.

The term "pigments" is intended to mean white or colored, mineral or organic particles, which are insoluble in an aqueous medium, and which are intended to color and/or opacify the resulting composition and/or deposit. These pigments may be white or colored, and mineral and/or organic.

The amount of pigment(s) preferably ranges from 2% to 25% by weight and more preferentially from 4% to 15% by weight relative to the total weight of the composition.

According to a particular embodiment, the pigments used according to the invention are chosen from mineral pigments.

The term "mineral pigment" is intended to mean any pigment that satisfies the definition in Ullmann's encyclopedia in the chapter on inorganic pigments. Among the mineral pigments that are useful in the present invention, mention may be made of zirconium oxide or cerium oxide, and also zinc oxide, iron oxide (black, yellow or red) or chromium oxide, manganese violet, ultramarine blue, chromium hydrate and ferric blue, titanium dioxide, and metal powders, for instance aluminum powder or copper powder. The following mineral pigments may also be used: $Ta_2O_5$, $Ti_3O_5$, $Ti_2O_3$, TiO, $ZrO_2$ as a mixture with $TiO_2$, $ZrO_2$, $Nb_2O_5$, $CeO_2$, ZnS.

The size of the pigment that is useful in the context of the present invention is generally greater than 100 nm and may range up to 10 μm, preferably from 200 nm to 5 μm and more preferentially from 300 nm to 1 μm.

According to a particular form of the invention, the pigments have a size characterized by a D[50] greater than 100 nm and possibly ranging up to 10 μm, preferably from 200 nm to 5 μm and more preferentially from 300 nm to 1 μm.

The sizes are measured by static light scattering using a commercial MasterSizer 3000® particle size analyzer from Malvern, which makes it possible to determine the particle size distribution of all of the particles over a wide range which may extend from 0.01 μm to 1000 μm. The data are processed on the basis of the standard Mie scattering theory. This theory is the most suitable for size distributions ranging from submicron to multimicron; it allows an "effective" particle diameter to be determined. This theory is notably described in the publication by Van de Hulst, H. C., *Light Scattering by Small Particles*, Chapters 9 and 10, Wiley, New York, 1957.

D[50] represents the maximum size that 50% by volume of the particles have.

In the context of the present invention, the mineral pigments are more preferentially chosen from metal oxides, in particular iron oxides and/or titanium dioxides, and more preferentially iron oxide pigments.

As mineral pigments that may be used in the invention, mention may also be made of nacres.

The term "nacres" should be understood as meaning colored particles of any form, which may or may not be iridescent, notably produced by certain molluscs in their shell, or alternatively synthesized, and which have a color effect via optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles, at the surface of which are superposed at least two successive layers of metal oxides and/or of organic colorants.

Examples of nacres that may also be mentioned include natural mica coated with titanium oxide, with iron oxide, with natural pigment or with bismuth oxychloride.

Among the nacres available on the market, mention may be made of the nacres Timica®, Flamenco® and Duochrome® (based on mica) sold by the company Engelhard, the Timiron® nacres sold by the company Merck, the Prestige mica-based nacres sold by the company Eckart, and the Sunshine® synthetic mica-based nacres sold by the company Sun Chemical.

The nacres may more particularly have a yellow, pink, red, bronze, orange, brown, gold and/or coppery color or tint.

As illustrations of nacres that may be used in the context of the present invention, mention may be made notably of the gold-colored nacres sold notably by the company Engelhard under the name Brilliant gold 212G® (Timica®), Gold 222C® (Cloisonne®), Sparkle Gold® (Timica®), Gold 4504® (Chromalite®) and Monarch gold 233X® (Cloisonne®); the bronze nacres sold notably by the company Merck under the name Bronze Fine® (17384) (Colorona®) and Bronze® (17353) (Colorona) and by the company Engelhard under the name Super bronze (Cloisonne®); the orange nacres sold notably by the company Engelhard under the name Orange 363C® (Cloisonne®) and Orange MCR 1010 (Cosmica®) and by the company Merck under the name Passion Orange® (Colorona) and Matte Orange® (17449) (Microns®); the brown nacres sold notably by the company Engelhard under the name Nu-antique copper 340XB (Cloisonne®) and Brown CL4509® (Chromalite®); the nacres with a copper tint sold notably by the company Engelhard under the name Copper 340A® (Timica®); the nacres with a red tint sold notably by the company Merck under the name Sienna Fine® (17386) (Colorona®); the nacres with a yellow tint sold notably by the company Engelhard under the name Yellow (4502) (Chromalite); the red nacres with a gold tint sold notably by the company Engelhard under the name Sunstone G012 (Gemtone); the pink nacres sold notably by the company Engelhard under the name Tan opale G005® (Gemtone®); the black nacres with a gold tint sold notably by the company Engelhard under the name Nu antique bronze 240 AB® (Timica®), the blue nacres sold notably by the company Merck under the name Matte blue (17433) (Microns®), the white nacres with a silvery tint sold notably by the company Merck under the name Xirona Silver®, and the golden-green pink-orange nacres sold notably by the company Merck under the name Indian summer (Xirona®), and mixtures thereof.

Among the pigments that may be used according to the invention, mention may also be made of those having an optical effect different from a simple conventional coloring effect, i.e. a unified and stabilized effect such as produced by conventional colorants, for instance monochromatic pigments. For the purposes of the invention, the term "stabilized" means lacking the effect of variability of the color with the angle of observation or in response to a temperature change.

For example, this material may be chosen from particles with a metallic tint, goniochromatic coloring agents, diffractive pigments, thermochromic agents, optical brighteners, and also fibers, in particular interference fibers. Needless to say, these various materials may be combined in order simultaneously to afford two effects, or even a novel effect in accordance with the invention.

The particles with a metallic tint that are usable in the invention are in particular chosen from:
  particles of at least one metal and/or of at least one metal derivative,
  particles comprising a monomaterial or multimaterial organic or mineral substrate, at least partially coated with at least one layer with a metallic tint comprising at least one metal and/or at least one metal derivative, and
  mixtures of said particles.

Among the metals that may be present in said particles, mention may for example be made of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo, Cr and mixtures or alloys thereof (for example, bronzes and brasses) are preferred metals.

The term "metal derivatives" denotes compounds derived from metals, especially oxides, fluorides, chlorides and sulfides.

Illustrations of these particles that may be mentioned include aluminum particles, such as those sold under the names Starbrite 1200 EAC® by the company Silberline and Metalure® by the company Eckart.

Mention may also be made of metal powders of copper or of alloy mixtures such as the references 2844® sold by the company Radium Bronze, metallic pigments, for instance aluminum or bronze, such as those sold under the names Rotosafe 700® from the company Eckart, silica-coated aluminum particles sold under the name Visionaire Bright Silver® from the company Eckart, and metal alloy particles, for instance the silica-coated bronze (alloy of copper and zinc) powders sold under the name Visionaire Bright Natural Gold from the company Eckart.

They may also be particles comprising a glass substrate, such as those sold by the company Nippon Sheet Glass under the name Microglass Metashine®.

The goniochromatic coloring agent may be chosen, for example, from interference multilayer structures and liquid-crystal coloring agents.

Examples of symmetrical multilayer interference structures that may be used in the compositions prepared in accordance with the invention are, for example, the following structures: $Al/SiO_2/Al/SiO_2/Al$, pigments having this structure being sold by the company DuPont de Nemours; $Cr/MgF_2/Al/MgF_2/Cr$, pigments having this structure being sold under the name Chromaflair® by the company Flex; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being sold under the name Sicopearl by the company BASF; $MoS_2/SiO_2/mica\text{-}oxide/SiO_2/MoS_2$; $Fe_2O_3/SiO_2/mica\text{-}oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2MO_2/mica/SnO$, pigments having these structures being sold under the name Xirona® by the company Merck (Darmstadt). By way of example, these pigments may be the pigments of silica/titanium oxide/tin oxide structure sold under the name Xirona Magic® by the company Merck, the pigments of silica/brown iron oxide structure sold under the name Xirona Indian Summer® by the company Merck and the pigments of silica/titanium oxide/mica/tin oxide structure sold under the name Xirona Caribbean Blue® by the company Merck. Mention may also be made of the Infinite Colors® pigments from the company Shiseido. Depending on the thickness and the nature of the various layers, different effects are obtained. Thus, with the $Fe_2O_3/SiO_2/Al/SiO_2/Fe_2O_3$ structure, the color changes from greenish gold to reddish gray for $SiO_2$ layers of 320 to 350 nm; from red to gold for $SiO_2$ layers of 380 to 400 nm; from violet to green for $SiO_2$ layers of 410 to 420 nm; from copper to red for $SiO_2$ layers of 430 to 440 nm.

As examples of pigments with a polymeric multilayer structure, mention may be made of those sold by the company 3M under the name Color Glitter®.

Examples of liquid-crystal goniochromatic particles that may be used include those sold by the company Chenix and also the product sold under the name Helicone® HC by the company Wacker.

These pigments may also be organic pigments.

The term "organic pigment" refers to any pigment that satisfies the definition in Ullmann's encyclopedia in the chapter on organic pigments. The organic pigment may notably be chosen from nitroso, nitro, azo, xanthene, quinoline, anthraquinone, phthalocyanine, metal complex type, isoindolinone, isoindoline, quinacridone, perinone, perylene, diketopyrrolopyrrole, thioindigo, dioxazine, triphenylmethane and quinophthalone compounds.

The organic pigment(s) may be chosen, for example, from carmine, carbon black, aniline black, melanin, azo yellow, quinacridone, phthalocyanine blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indolic or phenolic derivatives as described in patent FR 2 679 771.

These pigments may also be in the form of composite pigments as described in patent EP 1 184 426. These composite pigments may in particular be composed of particles comprising a mineral core at least partially coated with an organic pigment and at least one binder for fixing the organic pigments to the core.

The pigment may also be a lake. The term "lake" means insolubilized dyes adsorbed onto insoluble particles, the assembly thus obtained remaining insoluble during use.

The inorganic substrates onto which the dyes are adsorbed are, for example, alumina, silica, calcium sodium borosilicate, calcium aluminum borosilicate and aluminum.

Among the organic dyes, mention may be made of cochineal carmine. Mention may also be made of the products known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), D&C Blue 1 (CI 42 090).

An example of a lake that may be mentioned is the product known under the name D&C Red 7 (CI 15 850:1).

According to a particularly preferred mode of the invention, the composition comprises
a) water; and
b) a quaternary ammonium salt of hydroxyethyl cellulose and of 2,3-epoxypropyltrimonium having the INCI name: POLYQUATERNIUM-10; and
c) an anionic polymer of the sodium salt of methacrylic acid homopolymer type, having the INCI name: Sodium polymethacrylate; and
d) at least one iron oxide.

Additives

The compositions in accordance with the invention may also comprise at least one additive.

As additives that may be used in the compositions in accordance with the invention, mention may be made notably of antioxidants, preserving agents, hydrophilic gelling agents, fragrances, neutralizers, emollients, coalescers, plasticizers, moisturizers and vitamins, and mixtures thereof.

Needless to say, a person skilled in the art will take care to select the optional additional additives and/or the amount thereof such that the advantageous properties of the composition according to the invention are not, or are not substantially, adversely affected by the envisaged addition.

Cosmetic Compositions

The present invention also relates to a cosmetic composition comprising, in a physiologically acceptable medium, a composition as defined above.

The term "physiologically acceptable medium" is intended to denote a medium that is particularly suitable for applying a composition of the invention to the skin, notably the contour of the eyes, the eyelashes, the eyebrows and the contours thereof.

The physiologically acceptable medium is generally adapted to the nature of the support onto which the composition has to be applied, and also to the appearance under which the composition has to be packaged.

The composition according to the invention advantageously has a solids content of at least 42.0% by weight, and preferentially of at least 44.0% by weight relative to the total weight of the composition, or even from 45.0% to 60.0% by weight, relative to the total weight of the composition.

For the purposes of the present invention, the term "solids content" denotes the content of nonvolatile matter.

The amount of solids content (abbreviated as SC) of a composition according to the invention is measured using a Halogen Moisture Analyzer HR 73® commercial halogen desiccator from Mettler Toledo. The measurement is performed on the basis of the weight loss of a sample dried by halogen heating, and thus represents the percentage of residual matter once the water and the volatile matter have evaporated off. This technique is fully described in the machine documentation supplied by Mettler Toledo.

The measuring protocol is as follows:

Approximately 2 g of the composition, referred to hereinbelow as the sample, are spread out on a metal crucible, which is placed in the halogen desiccator mentioned above. The sample is then subjected to a temperature of 105° C. until a constant weight is obtained. The wet mass of the sample, corresponding to its initial mass, and the dry mass of the sample, corresponding to its mass after halogen heating, are measured using a precision balance. The experimental error associated with the measurement is of the order of plus or minus 2%.

The solids content is calculated in the following manner:

$$\text{Solids content (expressed in \% by weight)} = 100 \times \frac{\text{Dry mass}}{\text{Wet mass}} \quad [\text{Math 1}]$$

A composition according to the invention is advantageously creamy at 25° C. and atmospheric pressure. It is characterized by a viscosity of less than or equal to 40.0 Pa·s, or even preferably less than or equal to 35.0 Pa·s, or even less than or equal to 30.0 Pa·s, measured at 25° C. and atmospheric pressure by means of an RM100® Rheomat fitted with a no. 3 or 4 spindle, with a shear rate of 200 rpm and for 10 minutes.

Preferably, the viscosity of the compositions according to the invention ranges from 1.0 to 40 Pa·s., or even from 1 to 35 Pa·s, or even from 1 to 30 Pa·s.

According to one particular form of the invention, the composition is in the form of a direct emulsion comprising an aqueous continuous phase and a fatty phase dispersed in said aqueous phase. More particularly, the composition is in the form of a wax/water emulsion.

It may in particular be in the form of an eyelash product such as a mascara, an eyebrow product or a product for the contour of the eyes, such as an eyeliner.

More preferentially, the invention relates to a mascara. The term "mascara" is intended to mean a composition intended to be applied to the eyelashes. It may be a makeup composition for the eyelashes, a makeup base for the eyelashes (also called base coat), a composition to be applied over a mascara (also called top coat), or else a composition for the cosmetic treatment of the eyelashes. The mascara is more particularly intended for human eyelashes, but also for false eyelashes.

Applications

The present invention also relates to a process for coating keratin materials, in particular the skin, notably the contour of the eyes, eyelashes or eyebrows, and keratin fibers, such as the eyelashes and/or the eyebrows, comprising a step of applying to said keratin materials at least one cosmetic composition as defined above.

The present invention also relates to a process for coating keratin fibers, and in particular for making up the eyelashes, comprising a step of applying a cosmetic composition for coating keratin fibers as described above.

The present invention also relates to the use of a composition as defined above, for obtaining a deposit on the eyelashes which has a good black intensity.

Packaging and Application Assembly or Kit

The present invention also relates to an assembly, or kit, for packaging and applying a cosmetic composition for coating keratin fibers, comprising:
a device for packaging said cosmetic composition for coating keratin fibers as described above,
an applicator for said composition.

Said applicator may be integrally attached to a gripping member forming a cap for said packaging device. In other words, said applicator may be mounted in a removable position on said device between a closed position and an open position of a dispensing aperture of the device for packaging said composition.

An assembly for coating keratin fibers suitable for the invention may comprise an applicator suitable for applying said cosmetic composition for coating keratin fibers and, where appropriate, a packaging device suitable for receiving said composition.

Applicator

The applicator comprises means for smoothing and/or separating keratin fibers, such as the eyelashes or the eyebrows, notably in the form of teeth, bristles, spikes or other reliefs.

The applicator is arranged to apply the composition to the eyelashes or the eyebrows, and may comprise, for example, a brush or a comb.

The applicator may also be used for finishing of the makeup, over a region of the eyelashes or eyebrows that is made up or laden with the composition.

The brush may comprise a twisted core and bristles held between the turns of the core, or may be made in yet another way.

The comb is, for example, produced from a single part by molding of a plastic.

In certain exemplary embodiments, the application member is mounted at the end of a wand, which wand may be flexible, which may contribute to improving the comfort during application.

Packaging Device

The packaging device comprises a container for housing the composition for coating keratin fibers. This composition may then be withdrawn from the container by immersing the applicator therein.

This applicator may be firmly attached to a member for closing the container. This closing member may form a member for gripping the applicator. This gripping member may form a cap to be removably mounted on said container by any suitable means, such as screwing, click-fastening, push-fitting, etc. Such a container may thus reversibly house said applicator.

This container may be optionally equipped with a wiper suitable for removing surplus product taken up by the applicator.

A process for applying the composition according to the invention to the eyelashes or the eyebrows may also include the following steps:
  forming a deposit of the cosmetic composition on the eyelashes or the eyebrows,
  leaving the deposit on the eyelashes or the eyebrows, it being possible for the deposit to dry.

It should be noted that, according to another embodiment, the applicator may form a product container. In such a case, a container may, for example, be provided in the gripping member and an internal channel can internally connect this gripping member to the application members in relief.

Finally, it should be noted that the packaging and application assembly may be in the form of a kit, it being possible for the applicator and the packaging device to be housed separately in the same packaging article.

Throughout the application, the wording "comprising one" or "containing one" means "comprising at least one" or "containing at least one", unless otherwise specified.

Throughout the above description, unless otherwise mentioned, the term "between x and y" corresponds to an inclusive range, that is to say that the values x and y are included in the range.

EXAMPLES 1 to 3 AND C-EX1 to C-EX3

Examples 1 to 3 according to the invention comprising a pigment, the cationic polymer (CP) polyquaternium-10, the anionic polymer (AP) sodium polymethacrylate, and an anionic surfactant in a form neutralized by its cationic counterion, and counterexamples C-Ex1 to C-Ex3 (outside the invention), in which the cationic polymer and anionic polymer have been removed, were prepared. The concentrations of polyquaternium-10 and of sodium polymethacrylate are expressed in % by weight of polymer active material.

In the absence of the CP and of the AP, the concentrations of the waxes and those of the anionic surfactants were modified in each counterpart composition so as to obtain a stable formulation (no phase separation) having a solids content of the same order as that of the corresponding example of the invention and guaranteeing an equivalent level of final volume (solids content: 47.5-48.7%)

TABLE 1

| Phase | Ingredient (INCI) | C-Ex1 | Ex1 | C-Ex2 | Ex2 | C-Ex3 | Ex3 |
|---|---|---|---|---|---|---|---|
| (1) | Behenyl behenate (Kester Wax K-72 ®) | 13.9 | 12.4 | 13.8 | 12.4 | 13.9 | 12.4 |
| | Beeswax (GR B 889 ®) | 13.7 | 12.2 | 13.6 | 12.2 | 13.7 | 12.2 |
| | Carnauba wax (Cerauba T1 ®) | 3.5 | 3.1 | 3.5 | 3.1 | 3.5 | 3.1 |
| | Cetyl alcohol (Kalcol 6098 ®) | 1.9 | 1.7 | 1.9 | 1.7 | 1.9 | 1.7 |
| | Potassium cetyl phosphate (Amphisol K ®) | 5.6 | 5.0 | — | — | — | — |
| | Stearic acid | — | — | 5.6 | 5.0 | | — |
| | Sodium stearoyl glutamate (Amisoft HS 11 PF ®) | | | | | 5.6 | 5.0 |
| | Iron oxide CI 77499 | 8.0 | 8.0 | 8.0 | 8.0 | 8.0 | 8.0 |

TABLE 1-continued

| Phase | Ingredient (INCI) | C-Ex1 | Ex1 | C-Ex2 | Ex2 | C-Ex3 | Ex3 |
|---|---|---|---|---|---|---|---|
| (2) | Polyquaternium-10 (Celquat SC240C ®) | — | 2.8 | — | 2.8 | — | 2.8 |
| | Sodium polymethacrylate (Darvan 7-N ®) | — | 1.2 | — | 1.2 | — | 1.2 |
| | Aminomethyl propanediol (AMPD Ultra PC ®) | 0.2 | 0.2 | 1.33 | 1.2 | — | — |
| | Phenoxyethanol (Sepicide LD ®) | 0.5 | 0.5 | 0.5 | 0.5 | 0.5 | 0.5 |
| | Phenylethyl alcohol (Phenylethyl alcohol 00360220 ®) | 0.5 | 0.5 | 0.5 | 0.5 | 0.5 | 0.5 |
| | Water | qs 100 | qs 100 | qs 100 | qs 100 | qs 100 | qs 100 |
| | CP/(CP + AP) ratio in % by weight | 0 | 70 | 0 | 70 | 0 | 70 |
| | (CP + AP)/(CP + AP + Water) ratio in % by weight | 0 | 7.1 | 0 | 7.2 | 0 | 7.1 |
| | Solids in % by weight | 47.7 | 47.7 | 48.7 | 48.7 | 47.5 | 47.5 |
| | Appearance of the compositions | B | A | A | A | B | B |
| | Loss of polymer in % by weight after immersion of the dry deposit in water | 59.3 | 15.1 | 45.6 | 13.9 | 89.3 | 17.6 |
| | Appearance of the deposits after immersion in water | C | A | C | A | C | A |

Protocol for Preparing the Examples and Counterexamples

Mascara compositions in accordance with the invention are prepared as described below.

Preparation of Phase (1)

The starting materials were carefully weighed out beforehand using a balance (precision=0.01 g). The ingredients of phase (1) were melted in a jacketed heating pan in which an oil circulates, the temperature of which is controlled by means of a thermostatically-controlled oil bath. The nominal temperature was set at 90° C. After total melting, the pigment was introduced with stirring using a Rayneri blender. Stirring was maintained until a homogeneous preparation was obtained.

Preparation of Phase (2)

The water was preheated in an electric kettle to 95° C. The cationic polymer and the anionic polymer were mixed with hot water and then the preserving agents and the base were introduced into the water in a beaker at a temperature of 80° C. with stirring using a Rayneri blender.

Emulsification of Phases (1) and (2)

Phase (2) was poured into phase (1) with stirring for 5 minutes at 90° C. using a Rayneri blender. Phase (1)+(2) was then cooled to ambient temperature with stirring.

Appearance of the Composition

The appearance of the compositions is observed. The following notations A, B and C are given:
  A: Thick, black, smooth composition.
  B: Thick, black, matt composition.
  C: Heterogeneous composition with 2 liquid phases.

Protocol for Evaluating the Wear Property:

An amount (mi) of the compositions is applied to a glass substrate having an area of 5 cm×2.5 cm and left to dry for 1 hour. The dry sample was then immersed in a volume of 90 ml of water stirred with a magnetic stirrer at a speed of between 300 and 700 rpm. After 1 hour of immersion in water, the glass substrate was left to dry at ambient temperature (25° C.) and the amount (mf) of composition remaining on the dry deposit was measured. The wear property of each example is calculated by the loss of polymer after immersion in water expressed as a percentage by weight, with the following equation: (mi-mf)/mi.

The appearance of the deposits after immersion in water is observed. The following notations A, B and C are given:
  A: Deposit is intact on the support;
  B: Deposit exhibits slight makeup removal;
  C: Deposit exhibits considerable makeup removal.

The results of the tests showed that examples 1 to 3 according to the invention, having a CP/CP+AP weight ratio ranging from 40% to 70% and a (CP+AP/(CP+AP+Water) ratio ranging from 5% to 20%, had an excellent wear property (loss of polymer after immersion in water<20% and deposit intact after immersion in water: A) unlike the counterexamples C-Ex1, C-Ex2 and C-Ex3 not containing the CP/AP combination.

EXAMPLES C-EX4 TO C-EX6 (OUTSIDE THE INVENTION)

Counterexamples C-Ex4 to C-Ex6 outside the invention, which are identical respectively to examples 1, 2 and 3 according to the invention, but in which the anionic surfactant neutralized by its cationic counterion at 5% by weight has been replaced with a nonionic surfactant system at 5% by weight, were produced.

TABLES 2

| Phase | Ingredient (INCI) | C-Ex4 | C-Ex5 | C-Ex6 |
|---|---|---|---|---|
| (1) | Behenyl behenate (Kester Wax K-72 ®) | 12.4 | 12.4 | 12.4 |
| | Beeswax (GR B 889 ®) | 12.2 | 12.2 | 12.2 |
| | Carnauba wax (Ceruaba T1 ®) | 3.1 | 3.1 | 3.1 |
| | Cetyl alcohol (Kalcol 6098 ®) | 1.7 | 1.7 | 1.7 |
| | Steareth-2 | 2.5 | — | 2.5 |
| | Steareth-20 | 2.5 | — | — |
| | PEG-100 stearate | — | 5.0 | — |
| | Glyceryl behenate | — | — | 2.5 |
| | Iron oxide CI 77499 | 8.0 | 8.0 | 8.0 |

TABLES 2-continued

| Phase | Ingredient (INCI) | C-Ex4 | C-Ex5 | C-Ex6 |
|---|---|---|---|---|
| (2) | Polyquaternium-10 (Celquat SC240C ®) | 2.8 | 2.8 | 2.8 |
| | Sodium polymethacrylate (Darvan 7-N ®) | 1.2 | 1.2 | 1.2 |
| | Phenoxyethanol (Sepicide LD ®) | 0.5 | 0.5 | 0.5 |
| | Phenylethyl alcohol (Phenylethyl alcohol 00360220 ®) | 0.5 | 0.5 | 0.5 |
| | Water | qs 100 | qs 100 | qs 100 |
| | CP/(CP + AP) ratio in % by weight | 70 | 70 | 70 |
| | (CP + AP)/(CP + AP + Water) ratio in % by weight | 7.1 | 7.2 | 7.1 |
| | Appearance of the compositions | C | C | C |

The use of the nonionic surfactant system in the presence of the cellulosic cationic polymer and of the anionic polymer in counterexamples C-Ex4, C-Ex5, C-Ex6 outside the invention all resulted in unstable compositions constituted of two heterogeneous phases, contrary to their respective counterparts according to the invention 1, 2 and 3.

The invention claimed is:

1. A composition comprising, in a physiologically acceptable medium:
   a. water;
   b. at least one cellulosic cationic polymer (CP);
   c. at least one anionic polymer (AP) chosen from methacrylic acid homopolymer salts;
   d. at least one anionic surfactant comprising at least one cationic counterion;
   e. a fatty phase; and
   f. at least one pigment; wherein
   a weight ratio of the total amount of cellulosic cationic polymer(s)/the sum of the total amount of cellulosic cationic polymer(s) and of the total amount of anionic polymer(s) is from 40% to 80%; and
   a weight ratio of the sum of the total amount of cellulosic cationic polymer(s) and of the total amount of anionic polymer(s)/the amount of water is from 5% to 20%.

2. The composition of claim 1, wherein the water is present in a concentration ranging from 30% to 70% by weight relative to the total weight of the composition.

3. The composition of claim 1, wherein the cellulosic cationic polymer is selected from the group consisting of:
   quaternary ammoniums of hydroxy($C_1$-$C_4$)alkyl cellulose that has reacted with an epoxide substituted by a trimethylammonium group;
   hydroxy($C_1$-$C_4$)alkyl celluloses grafted by a methacryloylethyltrimethylammonium, methacrylamidopropyltrimethylammonium or dimethyldiallylammonium salt; and
   mixtures thereof.

4. The composition of claim 1, wherein the cellulosic cationic polymer is a quaternary ammonium salt of hydroxyethylcellulose and of 2,3-epoxypropyltrimonium having the INCI name: POLYQUATERNIUM-10.

5. The composition of claim 1, wherein the concentration of active material of cellulosic cationic polymer(s) is from 1.0% to 5.0% by weight relative to the total weight of said composition.

6. The composition of claim 1, wherein the anionic polymer is a sodium salt of methacrylic acid homopolymer, having the INCI name: Sodium polymethacrylate.

7. The composition of claim 1, wherein the concentration of active material of anionic polymer(s) is from 1.0% to 5.0% by weight relative to the total weight of said composition.

8. The composition of claim 1, wherein the pigment is a metal oxide.

9. The composition of claim 1, wherein the amount of pigment(s) is from 2% to 25% by weight, relative to the total weight of the composition.

10. The composition of claim 1, wherein the anionic surfactant(s) is selected from the group consisting of:
   i. alkyl phosphates;
   ii. alkyl sulfates;
   iii. alkyl sulfonates, alkylamide sulfonates, alkylaryl sulfonates, α-olefin sulfonates, paraffin sulfonates;
   iv. alkyl sulfosuccinates, alkyl ether sulfosuccinates, alkylamide sulfosuccinates; alkyl sulfosuccinamates;
   v. alkyl sulfoacetates;
   vi. acyl sarcosinates, acyl glutamates, acyl isethionates, N-acyl taurates and acyl lactylates;
   vii. alkylpolyglycoside carboxylic esters;
   viii. fatty acids;
   ix. alkyl-D-galactosiduronic acids;
   x. polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids; and
   xi. mixtures thereof.

11. The composition of claim 1, wherein the anionic surfactant(s) is (are) present in a total content of greater than or equal to 1% by weight relative to the total weight of the composition.

12. The composition of claim 1, wherein the cationic counterion(s) is (are) a cation of mineral origin the ammonium ion (NH4+) or organic cations.

13. The composition of claim 12, wherein the cationic counterion is an organic cation and said organic cationic counterion(s) is (are) selected from amines and amino alcohols.

14. The composition of claim 1, wherein the anionic surfactant is selected from the group consisting of:
   $C_{12}$-$C_{22}$ fatty acids;
   alkyl phosphates in a form neutralized by a cationic counterion of an alkali metal;
   acyl glutamates in a form neutralized by a cationic counterion of an alkali metal; and
   mixtures thereof.

15. The composition of claim 1, wherein the fatty phase is dispersed and comprises at least one wax, at least one pasty fatty substance and/or at least one oil.

16. The composition of claim 1, wherein the fatty phase is dispersed and comprises at least one wax selected from the group consisting of beeswax, carnauba wax, cetyl alcohol, behenyl behenate and mixtures thereof.

17. The composition of claim 1, in the form of an eyelash product, an eyebrow product or a product for the contour of the eyes.

18. An assembly, or kit, for packaging and applying a cosmetic composition for coating keratin fibers, comprising:
   a device for packaging said cosmetic composition for coating keratin fibers of claim 1, and
   an applicator for said composition.

19. A process for coating keratin materials, comprising applying to said keratin materials at least one composition of claim 1.

* * * * *